United States Patent [19]

Self

[11] Patent Number: 5,616,503
[45] Date of Patent: Apr. 1, 1997

[54] DETERMINATION OF HAPTENS

[76] Inventor: Colin H. Self, Little Callerton, 87 Runnymede Road, Ponteland, Northumbrie NE., Great Britain, 20 9H1

[21] Appl. No.: 256,525

[22] PCT Filed: Jan. 15, 1993

[86] PCT No.: PCT/GB93/00100

§ 371 Date: Jul. 15, 1994

§ 102(e) Date: Jul. 15, 1994

[87] PCT Pub. No.: WO93/14404

PCT Pub. Date: Jul. 22, 1993

[30] Foreign Application Priority Data

Jan. 17, 1992 [GB] United Kingdom .................. 9200957
May 26, 1992 [GB] United Kingdom .................. 9211158

[51] Int. Cl.$^6$ ............................................... G01N 33/543
[52] U.S. Cl. ..................... 436/518; 436/817; 436/822; 436/824; 436/825
[58] Field of Search ................................. 436/518, 523, 436/817, 822, 824, 825

[56] References Cited

U.S. PATENT DOCUMENTS

| | | | |
|---|---|---|---|
| 3,992,631 | 11/1976 | Harte | 436/815 |
| 4,376,110 | 3/1983 | David et al. | 436/548 |
| 4,813,924 | 3/1989 | Strahilevitz | 436/822 |
| 4,963,468 | 10/1990 | Olson | 436/574 |
| 5,030,558 | 7/1991 | Litman et al. | 436/822 |

*Primary Examiner*—David Saunders
*Attorney, Agent, or Firm*—Graham & James LLP

[57] ABSTRACT

A method of determining a hapten which comprises: (1) contacting the sample which contains or may contain the hapten with a first binding partner which binds the hapten; (2) separating the hapten bound to the first binding partner from material which is not bound by the first binding partner; (3) contacting the hapten bound to the first binding partner with a second binding partner which binds the hapten; and (4) assaying the hapten bound to a binding partner as is described. Kits are also described.

8 Claims, No Drawings

DETERMINATION OF HAPTENS

The present invention relates to the determination of haptens. More specifically this invention relates to a method of determination of haptens which has the benefit of high specificity to reagents used in such a method and to their preparation and to kits useful in such a method.

Many methods of determining haptens exist but a frequent problem encountered with present commercially employed method relates to lack of specificity. This is often because the binding partners employed bind not only the hapten being determined but also other haptens of related chemical structure. If one had infinite time and resource it should be possible to generate a binding partner that bound only the chosen hapten and none other. In practice this desirable state is not achieved and an unwelcome degree of cross reactivity can occur. The determination would be improved if the disadvantageous effects of this cross reactivity were reduced or eliminated. One method of "cleaning up" samples has been to treat the sample with an antibody which removes at least some cross reacting substances before determining the hapten. However, this can require assays to be carried out on treated and untreated samples to provide full data and is generally inconvenient. Clearly it would be an advantage, for example, if in a determination for one hapten such as a steroid hormone the effect of other related haptens such as other steroid hormones could be reduced or eliminated, or for example, if in the determination of a drug of abuse the effect of chemically related innocuous materials could be reduced and only one assay needed to be carried out.

A method has now been found which enables the determination of haptens to be carried out with a good degree of specificity and without the need for more than one assay to be performed:

The present invention provides a method of determining a hapten which comprises:

1. Contacting the sample which contains or may contain the hapten with a first binding partner which binds the hapten.
2. Separating the hapten bound to the first binding partner from material which is not bound by the first binding partner.
3. Separating the hapten bound to the first binding partner with a second binding partner which binds the hapten.
4. Assaying the hapten bound to a binding partner.

It will be understood that the first and second binding partners are non-identical. This means that they will have different cross reactivities so that the effect of interfering (i.e. cross reacting) substances will be reduced. Clearly the greater the difference in cross reactivity profile the better since the greater the difference the more specific the determination becomes. It is preferred that these two binding partners will be against different epitopes on the hapten. Although it is generally considered that a hapten can be bound by only one epitope at a time, the hapten can in effect have more than one epitope that can be bound at different times.

This may be understood by considering a steroid such as cortisol. Although cortisol can bind to only one antibody at a time, it is able to bind to different antibodies in different ways. Thus, for example, one antibody could bind to the C or D rings and their substituents whereas another antibody could bind to the A and B rings and their substituents. Similarly although digitoxin can bind only one antibody at a time it is capable of binding one antibody at the glycoside portion and another at the steroid portion at a different time. Such an explanation with respect to cortisol or digoxin is put forward to aid visualisation only and should not be viewed as a limitation to the generality of employing two different binding partners.

The sample employed may be or be derived from blood, serum, saliva, urine, tissue homogenate or any other convenient sample depending on the nature of the hapten. Thus, for example, when determining the amount of a steroid hormone or medicament, drug of abuse or the like, present in a patient, the sample may be derived as appropriate from the patient's blood, serum, saliva or urine and may be a simple diluate of such a fluid. Also, for example, if a pollutant is being determined in a water supply, food source or the like, the water supply or extract of the food source can be the sample.

The first binding partner may be any which binds the hapten. Normally this will be protein but any other binding partner will suffice as long as it can be used to isolate the hapten from the sample. The binding partner will most suitably be an antibody and will preferably be a monoclonal antibody.

When used herein the term "antibody" includes the whole immunoglobulin and to aggregates and fragments of the immunoglobulin. In certain cases it is more apt to use the whole immunoglobulin, for example for simplicity, whereas in other cases if is more apt to use a fragment such as the Fab, $Fab^1$, $F(ab^1)_2$, Fd, Fv, for example when the Fc portion could cause interference.

The first binding partner for the hapten will advantageously be as specific as can be readily obtained. Although the method of this invention in effect acts to improve the specificity of the first binding partner the more specific the first binding partner for the hapten the higher the overall specificity the method becomes. Thus it will be advantageous to employ a first binding partner that is of comparable specificity to those used in conventional immunoassays even though a reduction in its specificity can be accommodated by the methodology.

In favoured forms of this invention the first binding partner will be immobolised preferably by being on a solid surface. This greatly helps in the separation of the hapten bound to the first binding protein from contaminants derived from the sample which remain in the liquid phase. The solid surface may be that of a microtitre well or part thereof, a dip stick or part thereof, separatable particles such as magnetic particles, capillaries such as porous mats and the like. It is particularly surprising that even when the first binding partner is not in solution it can take part in the steps of this method described hereinafter.

The first binding partner maybe immobilized in any convenient manner, for example by simple absorption onto a surface or indirectly by binding to a material already on a surface. Such methods are well known in the art.

The separation of the solid and liquid phases will not occur until after sufficient time has elapsed to allow sufficient binding of hapten to first binding partner to occur. This first incubation time will usually be more than 30 seconds, more usually more than 5 minutes and most usually more than 10 minutes and will usually be less than 24 hours, more usually less than 12 hours and most usually less than 2 hours, for example, 20, 30, 60 or 90 minutes. Sometimes it is convenient to allow the incubation to occur overnight. If desired shaking or vibrating the system may be employed. If desired the temperature may be slightly elevated or depressed but usually it is sufficient to employ ambient temperature. The time required will depend upon the hapten first binding partner pair but the skilled worker will be able to determine the length of the incubation by using his knowledge of binding of haptens to binding partners.

Once the first incubation is over the separation of the solid and liquid phases may be by any suitable method such as by shaking or pipetting off the liquid phase, centrifugation, capillary separation or the like.

Once the separation is effected the solid may be washed in conventional manner. The washing solution may also contain such agents as salts, buffers, surfactants and the like in conventional manner. The skilled worker will be familiar with washing of bound materials after separation of the liquid phase.

The hapten bound to the first binding partner may be brought into contact with a second binding partner in any suitable manner. This may involve having the second binding partner in the liquid phase from which it may be retrieved, for example by absorption onto a solid surface, for example employing Protein A, an antibody, or the like to the second binding partner. Very surprisingly it has been found that an already immobilised secondary binding partner may be employed. In this preferred case both the first binding partner and the second binding partner are on solid surfaces connected by an aqueous phase. The solid surfaces employed may be as set out hereinbefore.

The assay of hapten bound to a binding partner may be any suitable method. Many methods of assay of haptens are commercially available and many more have been referred to in the patent and general literature.

It is preferred to assay hapten which has been bound to the secondary binding partner.

However, for the sake of convenience, these may be divided into two groups, namely those which measure the hapten bound to its first binding partner either directly or by difference and those which measure the hapten bound to its second binding partner either directly or by difference. By 'directly' it is meant that the measurement relates to the hapten and by 'indirectly' it is meant that the measurement relates to vacant sites on the binding partner.

Competitive assays for haptens are widely available and are suitable for use in this invention, for example those derived from Abbott under the trade names TDx or IMx.

Non-competitive assays for haptens such as those described in UK Patent Application No 88-27347.9 or in WO 85/04422 are also very apt for use in this invention.

The use of the second binding partner to in effect enhance release of the hapten from the first binding partner is particularly desirable as it removes the need to employ a further agent for this purpose. It is preferred therefore that either the second binding partner has a higher affinity for the hapten than the first binding partner as that it is employed in a greater amount or both. In a highly preferred aspect of this invention these components are arranged to allow an equilibrium to be set up between hapten bound to the first binding partner, free hapten in solution and hapten bound to the second binding partner. This is particularly advantageous when both the first and second binding partners are immobilized (for example bound to solid surfaces) but connected by an aqueous phase. This equilibrium will normally be set up after the hapten bound to the first binding partner has been separated from the original test solution and preferably washed.

Although it is very desirable that the method be as simple as possible and not employ an additional agent to aid release of the hapten from its first binding partner (and it is a great benefit that this can be achieved in this invention) the method of this invention can be surprisingly enhanced by use of an agent (in addition to the second binding partner) which aids release of the hapten from its first binding partner.

Thus in a preferred form this invention provides a method of determining a hapten which comprises:

1. Contacting the sample which contains or may contain the hapten to be determined with a first binding partner which binds the hapten.
2. Separating the hapten bound to the first binding partner from material which is not bound by the first binding partner.
3. Contacting the hapten bound to the first binding partner with an agent which aids release of the hapten from its first binding partner.
4. Either (a) contacting the released hapten with a second binding partner which binds the hapten in the presence or absence of the agent which aids release of the hapten from its first binding partner or (b) contacting the released hapten with a second binding partner which binds the hapten without contacting said second binding partner with the agent which aids release of the hapten from its first binding partner.
5. Assaying the hapten bound to a binding partner.

In this determination it is preferred that step 4(a) is employed. It is greatly preferred that the releasor does not bind to any significant extent to the second binding partner.

As a convenient shorthand the agent which aids release of the hapten from its first binding partner will be referred to herein as the "replacer". The bound form of the hapten is in equilibrium with the unbound form. This equilibrium can be displaced by including in the solution a replacer which can also become bound to the hapten's first binding partner. If this replacer is present in high enough quantity or binds firmly enough to the first binding partner than the equilibrium is forced in the direction of higher concentration of unbound hapten. Most aptly even in this aspect of the invention the method is constructed to utilize and equilibrium in which the second binding partner helps release the hapten from the first binding partner because hapten bound to the first binding partner, free hapten in solution and hapten bound to the second binding partner are connected by an aqueous phase.

Any material may be used as a replacer as long as it fulfils the requirement of adding release of the hapten from its first binding partner but in general two classes of agents are thought to be most useful. These are (a) antibodies which bind to the first binding partner and, more preferably, (b) analogues of the hapten.

Antibody replacers can in the most part for the sake of convenience be divided into two types, namely (i) anti-idiotypic antibodies of the first binding partners which are themselves antibodies and (ii) antibodies which bind to some feature of the first binding partner which is not the hapten binding site.

Anti-idiotypic antibody replacers may be obtained in any convenient manner. They are a particularly suitable class of replacers because they can be obtained with particularly high binding coefficients to the first binding partner but with little or no affinity for the second binding partner.

Antibodies which are not reactive against the binding site of the hapten on its first binding partner can also be of use. Such antibodies can be against the native binding partner or one modified, for example, by binding thereto a highly immunogenic material such as a nitro phenol or the like. When the first binding partner is an antibody a favoured form of the releasor antibody will be derived from a different species. Thus for example if a mouse is used as the source of the first antibody then the second antibody might be obtained from a rat, sheep, goat, horse or the like and may simply be raised against mouse antibodies in general.

Analogue replacers can in the most part for the sake of convenience be divided into two types, namely (1) simple analogues and (2) complex analogues.

Simple analogue replacers are molecules of similar structure to the hapten. Thus, for example, if the hapten is a steroid the simple analogue could be another steroid which has a structural difference from the hapten, for example the addition of a hydroxyl group, the absence of a double bond or the like.

In order to aid the release of the hapten from the first binding partner the simple analogue can be a similar molecule which is cross reactive with the first binding partner but not with the second. Thus, for example, if in the determination of a steroid with a first antibody there is known to be another steroid which interferes with the assay, then this would be a candidate releasor and the second binding partner would preferably be chosen to have a low affinity for the candidate releasor. Therefore, for example, if cortisol was the hapten to be determined and assays using its first binding partner alone were comprised by cross reactivity with progesterone then progesterone could be used as a releasor and preferably the second binding partner employed would have a low affinity for progesterone (to avoid the need to separate it from the hapten before the hapten was brought into contact with the second binding partner).

Complex analogues of the hapten are most aptly derivatives of the hapten or derivatives of its simple analogue. Although there will be many apt replacers of intermediate size, for example hapten conjugated with small organic groups such as fluorophores, such derivatives are often suitably large derivatives, for example conjugates with a protein or the like, for example a conjugate with bovine serum albumin. It can be advantageous to employ as complex analogue the immunogen which was used to raise the first binding partner in the case where that is an antibody.

The hapten bound to its first binding partner may be brought into contact with the releasor in any convenient manner. However, most suitably the releasor is present in solution and is introduced to the bound hapten (that is after incubation of sample and first binding partner). The solution may aptly contain salts, buffers, surfactants or other solubilising agents such as proteins if these are needed in the case of a releasor of low solubility.

The times for which contact is maintained may be as set out hereinbefore with respect to the binding of the hapten to its first binding partner.

After contact of the hapten bound to its first binding partner with the releasor, the released hapten is contacted with a second binding partner therefore. If the releasor is one which also becomes bound to the second binding partner then a separation step is employed with separates the hapten and releasor. If, as is preferred, the releasor is one which does not become bound to the second binding partner, no separation step is required.

Any suitable method of separating the hapten and releasor may be employed but in general if the releasor needs to be separated from the hapten it is most suitable that the releasor employed is of high molecular weight (for example an antibody or a hapten analogue bound to a high molecular weight material such as a protein) and that a separation method based on molecular weight is employed, for example centrifugation, percolation through a material which separates on the basis of molecular weight or the like.

Preferably the releasor employed does not interfere with the binding of the hapten to its second binding partner for example by binding to the second binding partner as this avoids the separation step.

It will be understood that terms such as "does not bind" means does not bind to a significant extent so as to cause an unacceptably high background. The skilled worker is used to such terminology since in immunodiagnostic systems absolutes rarely occur and low levels of residual binding almost always exist. However, the skilled worker will have no difficulty.

in order to avoid the separation step it will be desirable for the releasor to bind as little as possible with the second binding partner. The amount of reaction can be set as a % so that of the binding of hapten. For example, if the binding of the hapten is arbitrarily set at 100%, the binding of the releasor should aptly be less than 50%, more aptly less than 10%, most aptly less than 5%, favourably less than 1% and preferably less than 0.1%.

In order to avoid the separator step the releasor should bind much more strongly to the first binding partner than to the second binding partner. If the binding to the first binding partner is arbitrarily set at 100%, the releasor aptly should not bind to the second binding partner more than 20%, more aptly not more than 10%, most aptly not more than 5%, favourably less than 1% and preferably less than 0.1%.

When a releasor of low affinity for the second binding partner is employed it can be introduced at the same time as that second binding partner if desired.

Generally, the hapten to be determined by the method of this invention will have a molecular weight of not less than 100 daltons, more aptly not less than 200 daltons and favourably not less than 300 daltons. Generally the hapten to be determined by the method of this invention will have a molecular weight of not more than 1500, more aptly not more than 1000 and favourably not more than 600.

Haptens for determination include drugs of abuse other than alcohol medicaments (that is pharmacologically active agents suitably for medical use), pollutants including poisons and metabolic products.

Suitable drugs of abuse for determination by this method of this invention include those belonging to the opiate family, cocaine family, cannabiniol family and the like. Suitable medicaments include cardiac glycosides such as digoxin, aminoglycosides such as gentamycin, antineoplastic agents such as methotrexate, antihypertensive agents such as β-blockers such as atenalol, smooth muscle relaxants such as xanthines, for example, theophistine steroids such as cortisone, betamethasone, prendisolone or estrogen, anlagesics such as morphine, diacetylmorphine methadone, vitamins and the like. Suitable metabolic products include hormones such as thyroxine, steroidal hormones for example cortisol, cortisone, corticosterone, deoxycorticosterone, estradiol, estratriol, testosterone, progesterone and the like, cyclic AMP neopterin and other markers of cellular activity.

One group of haptens which have proved difficult to determine without interference from other members of the group is the steroids. Thus a preferred method of this invention is for the determination of a steroid.

In a particularly preferred aspect this invention provides a method of determining a steroid which comprises:

1. Contacting the sample containing the steroid with an immobilised first antibody therefor.

2. Separating said steroid bound to said immobilised first antibody from material not bound thereto.

3. Releasing said steroid bound to said immobilised first antibody by contact with an analogue of said steroid which binds to said first antibody.

4. Contacting the released steroid with a second antibody therefor which does not bind said analogue.

5. Assaying said steroid which has become bound to said second antibody therefor.

The steroid to be determined by this preferred method may be a medicament such as a cardiac glycoside, for example digoxin, or a steroidal anti-inflammatory agent such as betamethasone, cortisone, cortisol, triamoinilone, paramethose or a steroid involved in the investigation of or control of fertility or pregnancy such as estrogen, estradiol, estrone sulphate, estratriol, progesterone or ethisterone.

Particularly suitable steroids to be determined in this manner include medicaments such as digoxin and cortisol. The methods of this invention are particularly suitably used for determining hormones.

The present invention also provides kits useful for performing the method of this invention. A suitable kit according to this invention will comprise a first binding partner and a second binding partner for a hapten. Another suitable kit according to this invention will comprise a first binding partner for a hapten and an agent which aids release of the hapten from its first binding partner. A favoured kit according to this invention will comprise a first binding partner and a second binding partner for a hapten and an agent which aids release of the hapten from its first binding partner. Aptly the first binding partner present in the kit will be immobilised on a solid surface, for example in a microtitre well, capillary mat or the like which also forms part of the kit. Aptly the second binding partner will also be immobilized. The kits may, if desired, also contain buffers, surfactants, water or other useful materials for carrying out the method of this invention.

As previously indicated the first and second binding partner of the hapten must not bind it in the same manner (so that they will have different cross reactivities). Preferably the first and second binding partners are against different epitopes or structures. The binding partners will be selected empirically from available binding partners or produced by known methods, for example by raising an antibody against different epitopes or structures of the hapten. Clearly the second binding partner will be chosen to have low affinity for substances which cross react with the first binding partner.

To determine empirically whether a putative second binding partner is against a different epitope from a first binding partner, the first binding partner of the hapten may be bound to a solid surface, then exposed to the hapten and thereafter to the putative second binding partner. If the second binding partner is able to cause a reduction in the amount of hapten bound to the first binding partner then it may be selected as a candidate second binding partner. The greater the reduction in the amount of hapten retained by the first binding partner the more effective the second binding partner is likely to be when used in the methods of this invention.

When antibodies are used as first and second binding partner (as is preferred) they may be obtained by screening available antibodies or be specifically produced. On occasions they may be obtained during the preparation of a monoclonal antibody following immunization with a single hapten analogue such as its bovine serum albumin conjugate but more usually the two antibodies will result from immunisations with two different conjugates, for example where the conjugates are attached to the steroid nucleus by functions at "opposite ends" of the nucleus, for example in the case of cortisol, by conjugating large moieties through the 21-position or through the 3-position.

One test to show that a candidate binding partner of a hapten is suitable for investigation as a second binding partner is:

(1) the first binding partner is put on a well (2) radio-labelled analyte is added, incubated and the excess removed (3) the second binding partner to be tested is added in solution and incubated (4) the second binding partner under test is removed and either:

(5a) the second binding partner under test is measured for radioactivity (5b) the retained radioactivity of the well is determined and that removed by the second binding partner determined by difference from a well with no added second binding partner.

A binding partner is considered suitable for investigation as second binding partner for use with the first binding partner in the method of this invention if it binds the hapten well, for example, in excess of 60% of the hapten in fifteen minutes and preferably over 90% in less than five minutes. These particular figures are for guidance and the skilled man will be able to adopt suitable parameters having read the total disclosure herein. Obviously it will not bind well to interfering substances that cross react with the first binding partner.

The suitability of such binding partners (normally an antibody) can be confirmed in a multiple binding assay with the first binding partner and those that provide the required increase in specificity selected for use as second binding partner as follows:

1. The first antibody (or other first binding partner) is put on wells

2. Standard concentration ranges of specific analyte or cross-reactive substances are added, incubated and the wells washed 3. The candidate second antibody (or other first binding partner) is added and incubated 4. The second antibody is removed and assayed for the presence of analyte or cross-reactive substance by such means as conventional competititve immunoassay (or any other convenient assay)

5. The second antibody which in the method of this invention results in ready detection of the analyte but not cross-reactive substances are most suitable.

Since the second binding partner will be selected to have different cross reactivity to the first binding partner, a simple way of selecting an appropriate pair is to determine the cross reactivity of the first binding partner with respect to potentially interfering substances and to do the same with the second binding partner. Those second binding partners with different cross reactivities to that of the first binding partner may be employed with it in the method of this invention.

In the case were an agent which aids release of the hapten from its first binding partner is involved, demonstration that the first binding partner and a replacer are of use in the invention can employ any method which demonstrates the release of the hapten from the first binding partner, for example the following method:

(i) the first binding partner to be tested is bound to the wells of a microtitre strip (ii) the same amount of radio-labelled sample of the hapten is added to each well and incubated (iii) unbound radio-labelled material is removed (iv) the releasor to be tested is added to each well (time zero)

(v) from time zero and after short regular intervals (such as one minute intervals) separate wells are taken and their unbound contents removed (vi) the retained radioactivity in each well is determined.

The first binding agent and replacer are then considered as a pair suitable for use in the method of this invention if the releasor causes release of a significant amount of the hapten. For many purposes a release of 60% within ten minutes is acceptable and 90% within 5 minutes will be particularly good. The skilled worker will be able to make his selection after reading the full disclosures herein.

For chosen pairs, the releasor may then be tested against the second binding partner for possible interference. Again this may be done in many ways although a method directly analogous to that described for the selection of a suitable first binding partner and replacer may be used. In this method, the second binding partner simply replaces the first binding partner and, preferably, the replacer is added before the hapten as follows:

(i) the second binding partner to be tested is bound to the wells of a microtitre plate (ii) the replacer being tested is added to each well (iii) radio-labelled sample of the hapten is added to each well and incubated (typically for the time to be used in the final assay)

(iv) unbound radio-labelled material is removed (v) the retained radioactivity in each well is determined.

For a releasor to be of use in the method of this invention with a second binding partner then the addition of the releasor should preferably only show a small diminution, in any, (for example less than 20% and preferably effectively zero) of the binding of the labelled hapten. Again, having read the disclosures herein the skilled worker will be able to chose suitable materials.

Favoured releasors act to replace the analyte from its binding site in the first binding partner.

Antibodies for use herein may be raised in conventional manner or purified in conventional manner. Antibody fragments may likewise be prepared from the whole immunoglobulin in conventional manner.

To prepare a well, tube, cell, dipstick or the like which has the first and second binding partner on different parts of the surface a suitable method comprises introducing an amount of liquid containing the first binding partner, allowing the first binding partner to bind to the surface in which it is in contact, removing the liquid, if desired washing the surface, then either (a) if the surface has in effect been attenuated by the first binding partner, greater volume of solution of the second binding partner and thereafter incubating and optimal washing, or (b) add a solution of a coating agent which will prevent or minimise binding of the second binding partner, to cover at least the area binding the first binding partner, wash the surface, add a greater volume of solution of the second binding partner, incubate and thereafter optionally wash. In this method the positions of the first and second binding partner may be reversed if desired.

Alternatively a well, tube, cell or the like could be coated with first and second binding partner by laying it in one plane, coating part of the surface with one binding partner, thereafter coating other parts of surface with the other binding partner when the well, tube, cell or the like is held in a different plane. Also either or both first and second binding partners could be on separate surfaces, for example, one or both could be on particles so that they can be moved into position as desired.

Alternatively surfaces may be individually separately coated with different binding partners and then subsequently be brought together.

A favoured aspect of this invention a solid surface such as a well, tube, cell, dip stick or the like is provided to which is bound in one part a first binding partner for a hapten and in another part a second binding partner for the hapten.

The following Examples illustrate this invention:

EXAMPLE 1

Multiple Binding Assay for the Determination of Cortisol

The wells of Nunc microtitre plates are coated with a monoclonal antibody against cortisol conjugated to carrier in position 21 (Biogenesis 1991–92 catalogue reagent number 2330-5405 clone IN8/492) by placing 200 μl in coating buffer of 50 mM bicarbonate pH 9.3 (CB) at an antibody concentration of 2 μg/ml. After overnight incubation at room temperature the wells are shaken free of solution and glazed by the addition of 300 μl 0.2% bovine serum albumin (Sigma Chemical Co Ltd cat number A 3912) in CB left for 30 minutes and then washed four times with 50 mM Tris pH 7.4 containing 0.02% Tween 20 (TT). Standards of cortisol consisting of solutions containing various amounts of cortisol are then made up by means of stock solutions of 10 μg/ml being serially diluted 1:2 twelve times. Similarly, solutions containing materials to be tested for cross reactivity are made. 150 μl of each of these are placed into individual wells on the plate. The same volume of samples containing unknown concentrations of cortisol are also placed into other wells. The plate is incubated for one hour at room temperature and then washed four times with TT. Each well then receives 200 μl of a solution of cortisol 21-hemisuccinate:BSA in Tris buffer pH 7.4 and is incubated. A second plate is taken and coated and glazed as above but this time the antibody coating is to only 100 μl and it is done with a 1:1000 dilution of a cortisol polyclonal antibody raised against cortisol conjugated to carrier through its 3 position (Biogenesis cat number 2330-5115). 100 μl of the contents of each of the wells of the first plate are transferred to equivalent positions on the second plate and the plate incubated for a further hour at room temperature. 50 μl of a 1:200 dilution of cortisol (−3): antigen alkaline phosphatase conjugate (biogenesis cat number 2330-5604) is then mixed into each well and left for a further hour at room temperature. The wells are washed four times with TT. 100 μl of para-nitrophenol phosphate is then added to each well and the absorbance at 405 nm followed. Final readings from all wells are taken when the fastest developing well reaches an optical density of 2 optical density units. The standards are plotted with respect to their optional density and unknowns calculated. The degree of cross reactivity shown with the other standard materials is recorded as being superior than in immunoassay run with either antibody above.

EXAMPLE 2

Multiple Binding Assay for the Determination of Cortisol

The wells of Nunc microtitre plates are coated with a monoclonal antibody against cortisol conjugated to carrier in position 21 (Biogenesis 1991–92 catalogue reagent number 2330-5404 clone IN8/492) by placing 200 μl in coating buffer of 50 mM bicarbonate pH 9.3 (CB) at an antibody concentration of 2 μg/ml. After overnight incubation at room temperature the wells are shaken free of solution and glazed by the addition of 300 μl 0.2% bovine serum albumin (Sigma Chemical Co Ltd cat number A 3912) in CB left for 30 minutes and then washed four times with 50 mM Tris pH 7.4 containing 0.02% Tween 20 (TT). Standards of cortisol consisting of solutions containing various amounts of cortisol are then made up by means of stock solutions of 10 μg/ml being serially diluted 1:2 twelve times. Similarly, solutions containing materials to be tested for cross reactivity are made. 150 μl of each of these are placed into individual wells on the plate. The same volume of samples containing unknown concentrations of cortisol are also placed into other wells. The plate is incubated for one hour at room temperature and then washed four times with TT. Each well then receives 200 μl of a solution of cortisol 21-caprylate in Tris buffer pH 7.4 and is incubated. A second plate is taken and coated and glazed as above but this time the antibody coating is to only 100 μl and it is done with a 1:1000 dilution of a cortisol polyclonal antibody raised against cortisol conjugated to carrier through its 3 position (Biogenesis cat number 2330-5115). 100 μl of the contents of each of the wells of the first plate are transferred to equivalent positions on the second plate and the plate incubated for a further hour at room temperature. 50 μl of a 1:200 dilution of cortisol (−3): antigen alkaline phosphatase conjugate (biogenesis cat number 2330-5604) is then mixed into each well and left for a further hour at room temperature. The wells are washed four times with TT 100 μl of para-nitrophenol phosphate is then added to each well and the absorbance at 405 nm followed. Final readings from all wells are taken when the fastest developing well reaches an optical density of 2 optical density units. The standards are plotted with respect to their optional density and unknowns calculated. The degree of cross reactivity shown with the other standard materials is recorded as being superior than in immunoassay run with either antibody above.

EXAMPLE 3

Multiple Binding Assay for the Determination of Cortisol

The wells of Nunc microtitre plates are coated with a monoclonal antibody against cortisol conjugated to carrier in position 21 (Biogenesis 1991–92 catalogue reagent number 2330-5404 clone IN8/492) by placing 80 μl in coating buffer of 50 mM bicarbonate pH 9.3 (CB) at an antibody concentration of 10 μg/ml. After overnight incubation at room temperature the solutions are aspirated out of the wells and the wells washed four times with 50 mM Tris pH 7.4 containing 0.02% Tween 20 (TT) and then a 180 μl of 300 μl of 0.2% bovine serum albumin (Sigma Chemical Co Ltd cat number A 3912) in CB is carefully added into the bottom of the wells and left for 30 minutes, it is then carefully aspirated out after which 300 μl of the 1:1000 dilution of a polyclonal antibody against cortisol conjugated to carrier through its 3 position (Biogenesis cat number 2330-5115) is added and incubated for four hours at room temperature. The wells are washed four times with (TT). Standards of cortisol consisting of solutions containing various amounts of cortisol are then made up by means of stock solutions of 10 μg/mg being serially diluted with 1:2 twelve times. Similarly, solutions containing materials to be tested for cross reactivity are made. 80 μl of each of these are placed into individual wells on the plate. The same volume of samples containing unknown concentrations of cortisol are also placed into other wells. The plate is incubated for one hour at room temperature and then washed four times with TT. Each well then received 300 μl of a solution of cortisol 21-caprylate in Tris buffer pH 7.4 and is incubated. 20 μl of a 1:100 dilution of cortisol (−3): antigen alkaline phosphatase conjugate (biogenesis cat number 2330-5604) is then mixed into each well and left for a further hour at room temperature. The wells are washed four times with TT. 320 μl of para-nitrophenol phosphate is then added to each well and the absorbance at 405 nm followed. Final readings from all wells are taken when the fastest developing well reaches an optical density o 2 optical density units. The standards are plotted with respect to their optional density and unknowns calculated. The degree of reactivity shown with the other standard materials is recorded as being superior than an immunoassay run with either antibody above.

EXAMPLE 4

Multiple Binding Assay for the Determination of Cortisol

The wells of Nunc microtitre plates are coated with a monoclonal antibody against cortisol conjugated to carrier in position 21 (Biogenesis 1991–92 catalogue reagent number 2330-5404 clone IN8/492) by placing 200 μl in coating buffer of 50 mM bicarbonate pH 9.3 (CB) at an antibody concentration of 2 μg/ml. After overnight incubation at room temperature the wells are shaken free of solution and glazed by the addition of 300 μl 0.2% bovine serum albumin (Sigma Chemical Co Ltd cat number A 3912) in CB left for 30 minutes and then washed four times with 50 mM Tris pH 7.4 containing 0.02% Tween 20 (TT). Standards of cortisol consisting of solutions containing various amounts of cortisol are then made up by means of stock solutions of 10 μg/ml being serially diluted 1:2 twelve times. Similarly, solutions containing materials to be tested for cross reactivity are made. 150 μl of each of these are placed into individual wells on the plate. The same volume of samples containing unknown concentrations of cortisol are also placed into other wells. The plate is incubated for one hour at room temperature and then washed four times with TT. Each well then received 200 μl of a solution of cortisol 21-caprylate in Tris buffer pH 7.4 and is incubated. A second plate is taken and coated and glazed as above but this time the antibody coating is to only 100 μl and it is done with a solution of 2 μg/ml of a cortisol monoclonal antibody raised against cortisol conjugated to carrier through its 3 position (Biogenesis cat number 2330-5394 clone 2D1/40) purified from ascites fluid. 100 μl of the contents of each of the wells of the first plate are transferred to equivalent positions on the second plate and the plate incubated for a further hour at room temperature. 50 μl of a 1:200 dilution of cortisol (−3): antigen, alkaline phosphatase conjugate (biogenesis cat number 2330-5604) is then mixed into each well and left for a further hour at room temperature. The wells are washed four times with TT. 100 μl of para-nitrophenol phosphate is then added to each well and the absorbance at 405 nm followed. Final readings from all wells are taken when the fastest developing well reaches an optical density of 2.0 optical density units. The standards are plotted with respect to their optional density and unknowns calculated from the graph. The degree of cross reactivity shown with the other standard materials is recorded as being superior than an immunoassay run with either antibody above.

EXAMPLE 5

Multiple Binding Assay for the Determination of Cortisol

The wells of Nunc microtitre plates are coated with a monoclonal antibody against cortisol conjugated to carrier in position 21 (Biogenesis 1991–92 catalogue reagent number 2330-5404 clone IN8/492) by placing 80 µl in coating buffer of 50 mM bicarbonate pH 9.3 (CB) at an antibody concentration of 10 µg/ml. After overnight incubation at room temperature the solutions are aspirated out of the wells and the wells washed four times with 50 mM Tris pH 7.4 containing 0.02% Tween 20 (TT) and then a 180 µl of solutions of 300 µl 0.2% bovine serum album (Sigma Chemical Co Ltd cat number A 3912) in CB carefully added into the bottom of the wells and left for 30 minutes, again carefully aspirated out after which 260 µl of a 40 µg/ml solution of a monoclonal antibody against cortisol conjugated to carrier through its 3 position (Biogenesis cat number 2330-5394—clone 2D1/40) purified from its ascites is added and incubated for four hours at room temperature. The wells are washed four times with (TT). Standards of cortisol consisting of solutions containing various amounts of cortisol are then made up by means of stock solutions of 10 µg/ml being serially diluted 1:2 twelve times. Similarly, solutions containing materials to be tested for cross reactivity are made. 80 µl of each of these are placed into individual wells on the plate. The same volume of samples containing unknown concentrations of cortisol are also placed into other wells. The plate is incubated for one hour at room temperature and then washed four times with TT. Each well then receives 280 µl of a solution of cortisol 21-caprylate in Tris buffer pH 7.4 and is incubated. 20 µl of a 1:100 dilution of cortisol (−3): antigen, alkaline phosphatase conjugate (biogenesis cat number 2330-5604) is then mixed into each well and left for a further hour at room temperature. The wells are washed four times with TT. 320 µl of paranitrophenol phosphate is then added to each well and the absorbance at 405 nm followed. Final readings from all wells are taken when the fastest developing well reaches an optical density of 2 optical density units. The standards are plotted with respect to their optical density and unknowns calculated. The degree of cross reactivity shown with the other standard materials is recorded as being superior than an immunoassay run with either antibody above.

EXAMPLE 6

Low cross-reactivity immunoassay for cortisol based on the use of a sequestration (second) binding partner.

(I) Selection of a Candidate Secondary Binding Pattern for Use in the Assay

A purified murine monoclonal antibody raised against cortisol (-3-0-CMO) bovine serum albumin (fbp) coated onto microtitre well strips by placing 200 µl of a solution of 5 µg/ml in 50 mM bicarbonate coating buffer pH 9.3 (CB) in each well and leaving overnight at 4° C. The next day a solution of 0.2% hydrolysed caseine in CB is left for one hour at room temperature in the wells and then removed and the wells washed four times with 50 mM Tris pH 7.4 containing 0.02% Tween 20 (TT). A solution of tritiated cortisol (Amersham International product code TRK 407) is made up to contain 100,000 cpm. 200 µl of aliquots of this are put into the coated microtitre wells and incubated for one hour at room temperature. The solution is then shaken out and the wells washed four times with TT. 200 µl of phosphate buffered saline containing 2 µg of putative sbp antibody under test is then added to duplicate wells other wells receiving the same amount of an antibody unrelated to the test. The solutions are incubated overnight at room temperature and then taken off and the wells washed four times in TT. The wells are separated and their retained radioactivity determined. An antibody which gives rise to the removal of more than 80% of the radioactivity from the well is then taken and used as a candidate sequestrating antibody as below.

(II) Use of the Secondary Binding Partner in the Assay of Cortisol

The same fbp and sbp are used as described above.

Microtitre wells are coated with the fbp as in the previous example. A range of cortisol standards from 100 ng/ml down in ten-fold doubling dilution are made as are solutions of pregnenolone and corticosterone. 'Unknown' samples are taken containing cortisol with various amounts of pregnenolone and corticosterone. 200 µl of each of these are put into duplicate wells and incubated for one hour at room temperature. The solutions are shaken out and the wells washed four times with TT. 200 µl containing 2 µg of the sbp is added to each well and incubated overnight at room temperature. The 'resulting solutions' are taken from each well and kept separate. The amount of analyte or cross-reactive substance associated with the sbp is then determined by means of the Selective Antibody technology (UK Patent Application Number 88-27347.9; Barnard, G & Kohen, F (1990) Clinical Chemistry, 36, 1945–1950) by means of antibodies raised against the sbp.

Alternatively, the analyte and cross reactivity is determined by means of a conventional competitive immunoassay as follows:

180 µl of each 'resulting solution' is placed into wells of a microtitre plate previously coated with Protein A and incubated at room temperature for 30 minutes. The solutions are removed and the plate washed four times with TT. 200 µl of a 1:100 dilution of cortisol (-3-0-CMO) alkaline phosphatase conjugate is then added and incubated for one hour at room temperature. The solution is discarded and the wells washed four times with TT. 200 µl of 10 mM para-nitrophenol phosphate in 50 mM bicarbonate buffer pH 10.3 containing 3.3 mM para-nitrophenol phosphate in 50 mM bicarbonate buffer pH 10.3 containing 3.3 mM MgCl2 is then added to each well and the optical density of the wells recorded at 405 nm until the fastest developing well reaches an optical density of 2.0 OD units. The optical densities of all wells are then recorded.

A graph of optical density against cortisol concentration is drawn and the degree of cross reactivity of prenenolone and corticosterone calculated. Those second antibodies which give rise to a reduced degree of cross reactivity than that found with the same antibodies when used in conventional competititve immunoassays. From the standard curve the concentration of cortisol in the unknowns is calculated for those assays run with the secondary antibodies showing reduced cross-reactivity.

EXAMPLE 7

Low Cross-Reactivity Immunoassay for Cortisol Based on the Use of a Sequestrating Binding Partner The previous example is repeated but the sequestrating antibody (that is the second binding partner) is a polyclonal antibody raised against cortisol-21-hemisuccinate-HSA and the 'resulting solution' assayed by means of competitive immunoassay.

EXAMPLE 8

A 96-well microtitre plate (Dynatech, M129 IV) was coated by the addition of 200 µl of 2 µg/ml of a monoclonal antibody raised against cortisol linked to bovine serum albumin (BSA) through the 21-cortisol position (Biogenesis, 1991 Cat Number 2330-5404) in coating buffer of 50 mmol carbonate-biocarbonate pH 9.6 (CB). The solution was left overnight at 4°. The solutions were then shaken out of the wells and replaced with 300 µl of a 0.5% BSA (Sigma Chem Co Ltd, A-7030) solution in CB. This was left for 30 mins and the plates were washed with a solution of 50 mM TRIS pH 7.4 containing 0.02% Tween Twenty (TT). Standard cortisol (Sigma Chem Co Ltd, 1992 Cat Number H4001) dilutions consisting of 100 µg/ml, 10 µg/ml, 1 µg/ml and a zero blank were made up using 50 mmol Tris-HCL/0.2% BSA, pH 7.4. 200 µl of these were added separately to independent wells and incubated for 1 hr at room temperature. The wells were washed 4 times with TT. A polyclonal antiserium raised against cortisol at the 3 position conjugated to BSA (Biogenesis, 1991 Cat Number 2330-5115) was then diluted 1:5000 in 50 mmol Tris-HCL, 0.2% BSA, pH 7.4 and 200 µl of this added to each well. The plate was then continuously shaken for 2 hrs after which 100 µl of each dilution was added to independent wells on a second plate. This second plate had been previously coated at 4° C. overnight with 100 µl in each well of 10 µg/ml protein A (Sigma Chem Co Ltd, 1992 Cat Number P-6031) solution in CB followed by removal of the solutions and the addition of 300 µl of 0.5% BSA in CB which was incubated for 30 min at room temperature followed by the plate being washed 4 times with TT. After this plate had received 100 µl of each solution from plate 1, it was incubated 2 hrs with continuous shaking followed by removal of the solutions and the wells being washed 4 times with TT. Into each well was then put 100 µl of a 1 in 200 dilution of a conjugate of cortisol with alkaline phosphatase linked through the cortisol 3 position (Biogenesis, 1991 Cat Number 2330-5604). This was left for 1 hr at room temperature and then the plate washed 4 times with TT. Each well then received 200 µl of a 5 mmol solution of para-nitrophenylphosphate (BDH, 1992 Cat Number 10800) in 50 mmol carbonate-bicarbonate buffer pH 10.3 containing 3.3 mmol $MgCl_2$. The plate was then incubated at room temperature and the absorbances of the wells followed at 405 nm. These were recorded when they had reached suitable levels as shown in Table 1.

TABLE 1

| Cortisol ug $mL^{-1}$ | absorbance at 405 nm |
|---|---|
| 0 | 1736 |
| 1 | 1484 |
| 10 | 1433 |
| 100 | 1222 |

Unknown samples, standards and potentially crossreactive materials are run in analogous fashion for the highly specific determination of cortisol.

EXAMPLE 9

A 96-well microtitre plate (Dynatech, M129 V) (A) is coated by the addition to each well of 200 µl of a 2.5 µg/ml of a monoclonal antibody against digoxin in carting buffer and left overnight at room temperature. A second microtitre plate (B) is coated with a solution of Protein A at a concentration of 10 µg/ml in coating buffer and left for two hours at room temperature and then overnight at 4 centigrade.

After incubation the coating solution is removed from plate (A) and the wells blocked by the addition of 200 µl 0.5% BSA in coating buffer to each well and left for 3 hr at room temperature. It is washed at 100 µl of a range of solutions of digoxin and potentially cross-reactive substances from 1 µg/ml to 10 pg/ml in Tris-BSA are then added to separate wells and incubated for 1 hr at room temperature. The plate is again washed and a 100 µl of a solution of the second anti-digoxin monoclonal antibody with a different cross-reactivity to the first is added in Tris-BSA at a concentration of 10 µg/ml and incubated for 1 hr at room temperature. The contents of plate (A) are then transferred to plate (B) and incubated for 2 hrs at room temperature, overnight at 4 centigrade and then two hours at room temperature. Plate (B) is then washed and 100 µl of IgG 2a (UPC10) at 50 µg/ml is added and incubated for 1 hr at room temperature. The plate is washed and to each well was added 100 µl of 1:10 dilution of serum-free tissue culture fluid containing a specific monoclonal antibody selective blocker against the second anti-digoxin antibody and incubated for 1 hr at room temperature.

The plate is washed and 100 µl of a 1:100 dilution of an alkaline phosphatase-labelled selective antibody against the second anti-digoxin antibody is added and left for 1 hr at room temperature. The plate is again washed and 100 µl of para-nitrophenol substrate is added in 50 mM bicarbonate buffer pH 10.3. The optical densities of each well are monitored at 405 nm.

As the system has taken advantage of two different monoclonal anti-digoxin antibodies of different cross-reactivities that of the system is less than that with assays employing either monoclonal antibody alone and it is used for the highly specific assay of samples for digoxin by the above method but by adding the unknown samples in place of the digoxin or cross-reactive standards.

I claim:

1. A method of determining a hapten in a sample which comprises:

(1) contacting the sample which contains or may contain the hapten with a first binding partner which binds the hapten; (2) separating the hapten bound to the first binding partner from material which is not bound by the first binding partner; (3) thereafter contacting the hapten bound to the first binding partner with a second binding partner which binds the hapten with release of the first binding partner from the hapten; and (4) assaying the hapten bound to the second binding partner.

2. A method is claimed in claim 1 wherein the first binding partner is a monoclonal antibody against a first epitope of the hapten and the second binding partner is a monoclonal antibody against a different epitope of the hapten.

3. A method as claimed in claim 1 wherein the hapten is a steroid.

4. A method as claimed in claim 1 wherein the hapten is cortisol.

5. The method of claim 1 wherein the first and second binding partners recognize different epitopes of the hapten.

6. A method of determining a hapten which comprises:

(1) contacting a sample which contains or may contain the hapten with a first binding partner which binds the hapten; (2) separating the hapten bound to the first binding partner from material which is not bound by the first binding partner; (3) contacting the hapten bound to the first binding partner with an agent which aids releases of the hapten from the first binding partner (4) contacting the hapten released from the first binding partner with a second binding partner which binds the hapten in the presence or absence of the agent which aids release of the hapten from the first binding partner; and (5) assaying the hapten bound to the second binding partner.

7. A method as claimed in claim 6 wherein the agent is an analogue of the hapten.

8. A method of determining a hapten which comprises:

(1) contacting a sample which contains or may contain the hapten with a first binding partner which binds the hapten; (2) separating the hapten bound to the first binding partner from material which is not bound by the first binding partner; (3) contacting the hapten bound to the first binding partner with a second binding partner which binds the hapten; and (4) assaying the hapten bound to the second binding partner wherein an equilibrium is employed between hapten bound to the first binding partner, free hapten in solution and hapten bound to the second binding partner.

* * * * *